United States Patent [19]
Hunt

[11] Patent Number: 5,973,778
[45] Date of Patent: Oct. 26, 1999

[54] METHOD OF MONITORING A THIN FILM OF POLYIMIDE MATERIAL USING SURFACE SPECTROSCOPY

[75] Inventor: Jeffrey H. Hunt, Chatsworth, Calif.

[73] Assignee: Boeing North American, Inc., Seal Beach, Calif.

[21] Appl. No.: 08/730,832

[22] Filed: Oct. 17, 1996

Related U.S. Application Data

[63] Continuation-in-part of application No. 08/200,100, Feb. 22, 1994, Pat. No. 5,623,341.

[51] Int. Cl.$^6$ ........................................................ G01J 3/00
[52] U.S. Cl. ......................................... 356/300; 356/237.2
[58] Field of Search .................................... 356/300, 237, 356/237.1–237.6; 156/626.1, 643.1, 627.1, 345; 118/712; 427/10; 349/187, 192

[56] References Cited

U.S. PATENT DOCUMENTS

| | | |
|---|---|---|
| 5,294,289 | 3/1994 | Heinz et al. . |
| 5,399,664 | 3/1995 | Peng et al. . |
| 5,534,201 | 7/1996 | Summers et al. . |

OTHER PUBLICATIONS

Hunt et al, "Observation . . . Generation" vol. 133, No. 3 Chemical Physics Letters Jan. 1987 pp. 189–192.
Shen et al "Probing Liquid Crystals . . . Processes" Proceedings Jul. 15–18, 1986.
Hsiung et al "Polar Ordering . . . Study", pp. 3127–3130 Chemical Physics vol. 87 No. 5 Sep. 1987.
Hsiung et al "Probing . . . Generation" pp. 4303–4309 American Physical Society Physical Review A vol. 34, No. 5 Jan. 1986.
Heinz et al "Surface Studies . . . Generations" Trends in Analytical Chemistry vol. 8 No. 6 1989 pp. 235–242.

*Primary Examiner*—K P Hantis
*Attorney, Agent, or Firm*—Harry B. Field

[57] ABSTRACT

A method for monitoring a thin film of polyimide material on the surface of a liquid crystal display uses nonlinear second-order surface spectroscopy to monitor the condition of a surface. Electromagnetic radiation is directed towards the surface and the second harmonic or other second-order frequency responses are monitored to detect the state of the surface. Preferably, a laser, input optics and output optics are utilized to create the second-order frequency response that is detected.

19 Claims, 4 Drawing Sheets

5,973,778

METHOD OF MONITORING A THIN FILM OF POLYIMIDE MATERIAL USING SURFACE SPECTROSCOPY

This application is a continuation in part of the allowed application Ser. No. 08/200,100 filed on Feb. 2, 1994 now U.S. Pat. No. 5,623,341.

1. Field of the Invention

The present invention relates to monitoring the properties of a thin film surface, specifically, monitoring a thin film of liquid crystal or polyimide material using electromagnetic radiation. In the most generic sense, surface means the interface between any two dissimiliar media. It can be between a gas and a solid, a vacuum and a solid, a gas and a liquid, between two liquids, between a liquid and a solid, or between two solids, etc.

2. BACKGROUND OF THE INVENTION

At an interface between two media it is helpful to be able, at different times and/or for different applications, to determine the physical, chemical, mechanical, and molecular properties of that interface. A nonintrusive, nondestructive method to investigate the interface is desirable. Because the method should not impose restrictions based on the particular environment around that interface, an electromagnetic radiation technique utilizing visible light, ultraviolet light, infrared, x-rays, radio frequencies or any other electromagnetic radiation may be used. The frequency at which one or the other interface media is transparent will determine the type (e.g., visible, ultraviolet, etc.) of signal chosen to provide a surface specific response. For example, linear reflection optical techniques (i.e., the output frequency equals the input frequency), do not provide what is called a surface specific response.

2.1 Prior Approaches

Other techniques can be used to analyze molecular properties or behavioral properties at an interface. Unfortunately, many of them may be characterized as environmentally limited in their application. For example, such techniques may be applied only in ultra-high-vacuum, which means that nothing with a liquid or gas interface may be tested. Moreover to inspect a vacuum-solid interface, the material to be examined must be placed in a high vacuum chamber. This can often be either slow, expensive or impractical depending on the size of the particular material in question.

Other techniques which exist may require that the interface be placed in other environments such as between two solids, in which case it may be necessary to destroy the particular material to be studied. Still other techniques may require either fabrication of very exotic detection means or require signal integration times which makes them unusable in any sort of real time industrial scenario.

2.2 Historical Development

In nonlinear optics, outputs are produced at sum, difference or harmonic frequencies of the input(s). Using second-order nonlinear optical surface spectroscopy to study a surface was originally proposed in the 1960's in "Light Waves at the Boundary of Nonlinear Media" by Bloembergen and P. S. Pershan, The Physical Review, 128, p. 193 (1962). Experimental work involving second harmonic generation was also performed. However, because lasers at the time were comparatively feeble, impractical, slow, etc., there was little subsequent work done on the development of second harmonic generation or, more generally, second-order nonlinear optical (NLO) processes at surfaces until considerably later.

More recently, researchers have reviewed NLO processing and concluded that lasers had developed enough that they could be used for studying the physical and chemical properties of surfaces and interfaces. For example, a theoretical study of the physics of the interface and not its engineering aspects has been performed. See Annual Review of Materials Science, "Surface Second Harmonic Generation", Vol. 16, pp. 69–86 (1986).

3. SUMMARY OF THE INVENTION

NLO techniques can be used to solve pragmatic problems that occur in industry (e.g., monitoring of a thin film). A method in accordance with the invention uses a second-order nonlinear optical technique to probe an interface between two media. In particular, second harmonic generation of a single input or sum-frequency generation of multiple inputs may be utilized.

The fact that a second-order process is used means that the reflected signal can only originate at the interface and not by the material through which the optical probe signal is traveling nor from the reflecting bulk. Thus, the reflected signal is generated from the two or three molecular layers actually at the interface, which can make the reflected (output) signal generated highly surface specific. Consequently, any changes at the interface will result in a very strong change in the intensity of the reflected optical signal.

Frequency generation may include a variety of techniques. For example, if two frequency inputs are used, $f_1$ and $f_2$, the output signal may be $f_1+f_2$ (sum frequency generation). Alternatively, the analyzed output signal may be a difference frequency generation of $f_1-f_2$. A method in accordance with the invention uses a second-order frequency generation process to monitor a thin film of liquid crystal or polyimide material on the surface of a liquid crystal display.

4. BRIEF DESCRIPTION OF DRAWINGS

Figure 4:
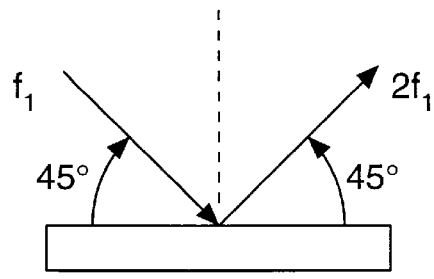
Figure 4A:
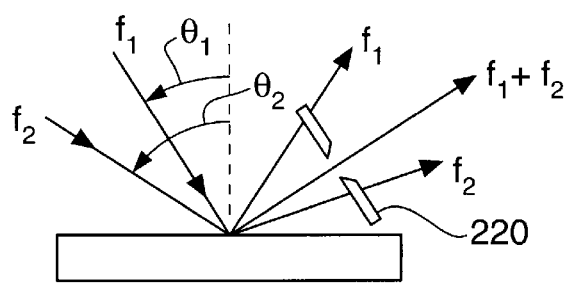
Figure 4B:
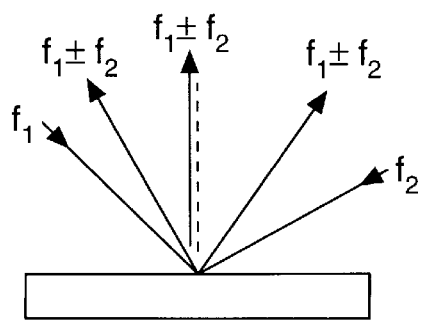

FIGS. 4, 4A, and 4B are diagrams of various input light beam configurations that may be used according to the present invention.

Figure 5:
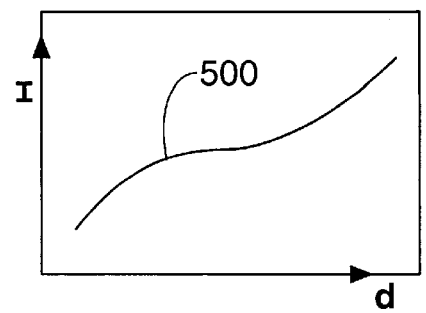

FIG. 5 is a graph of a detected signal intensity that varies with sample positions.

Figure 5A:
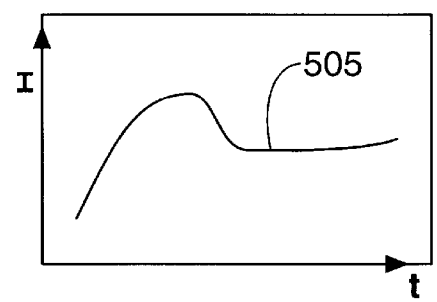

FIG. 5A is a graph of a detected signal intensity that varies over time.

Figure 5B:
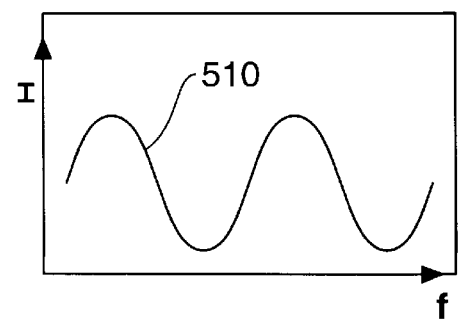

FIG. 5B is a graph of a detected signal intensity that varies with frequency.

Figure 6A:
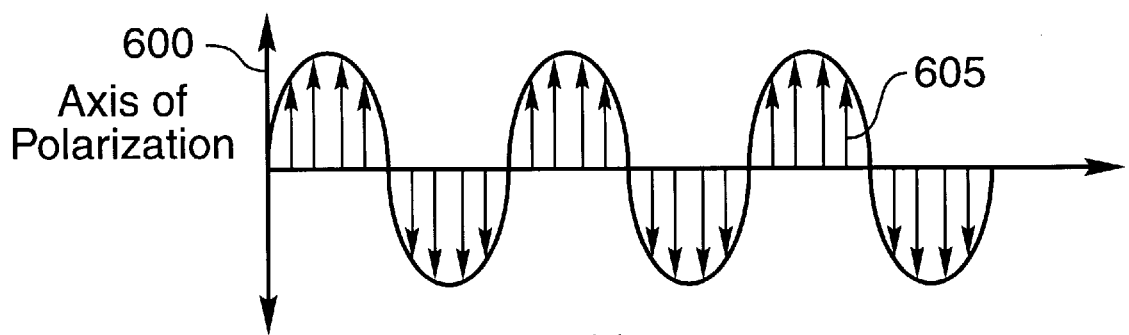
Figure 6B:
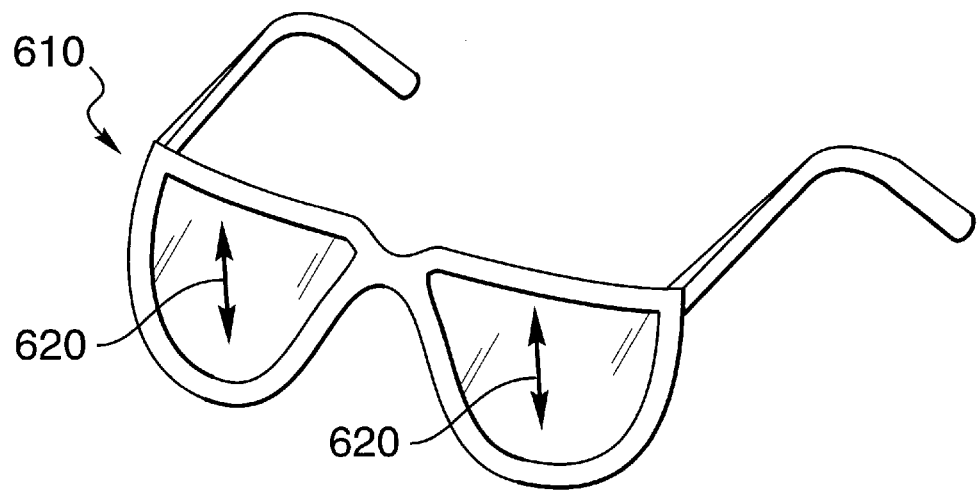
Figure 6C:
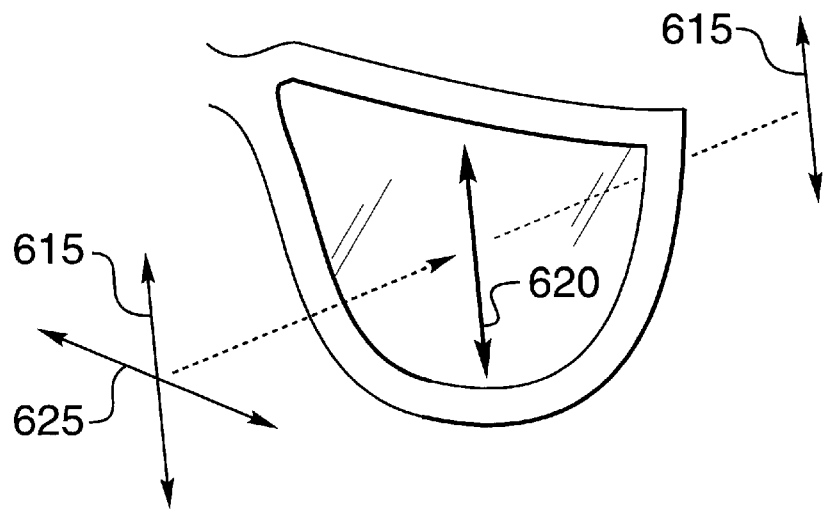

FIGS. 6A, 6B, and 6C illustrate the relationship between polarization and an electric field.

Figure 7:
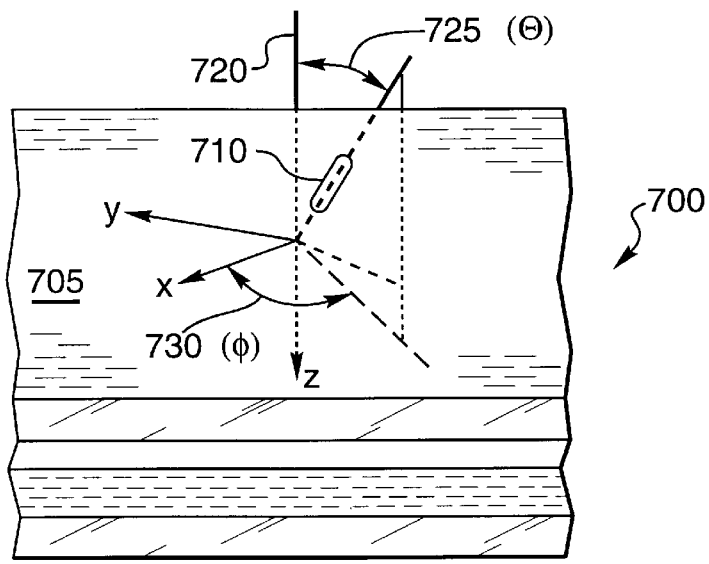

FIG. 7 illustrates a cross-sectional view of a liquid crystal display.

Figure 8A:
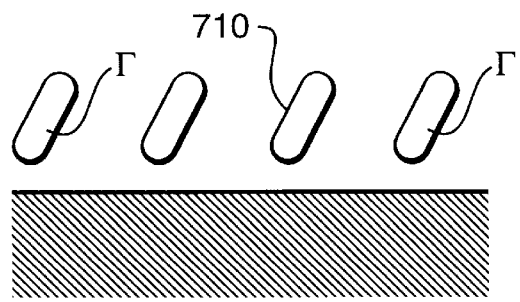
Figure 8B:
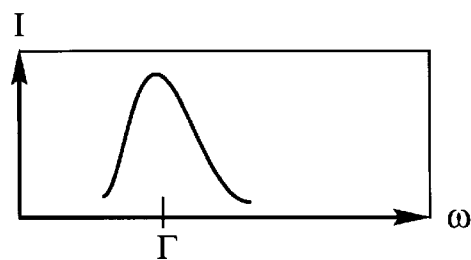

FIGS. 8A and 8B illustrate molecules and their resonance when the molecules are not bound to the surface.

Figure 8C:
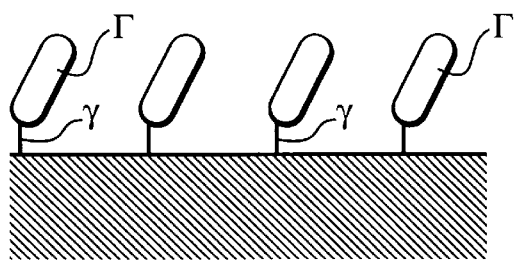
Figure 8D:
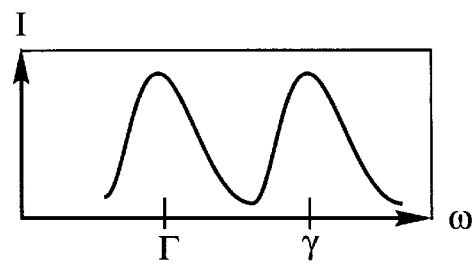

FIGS. 8C and 8D illustrate molecules and their resonance when the molecules are bound to the surface.

5. DETAILED DESCRIPTION OF SPECIFIC EMBODIMENTS

Illustrative embodiments of the invention are described below as it might be employed in the construction of a method of monitoring of the binding and alignment of a thin film, such as a thin film of liquid crystal or polyimide material in a liquid crystal display (LCD). In the interest of clarity, not all features of an actual implementation are described in this specification. It will of course be appreciated that in the development of any such actual embodiment numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill having the benefit of this disclosure.

5.1 System Schematic

Figure 1:
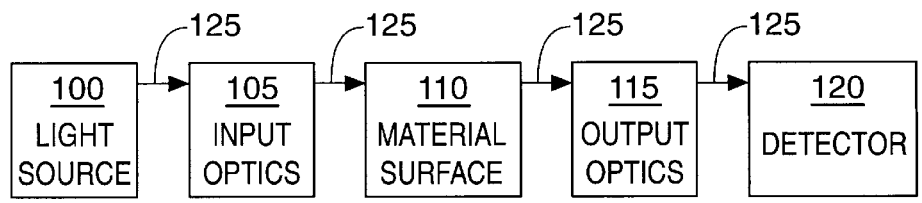
FIG. 1 is a block diagram representation of a system schematic according to the present invention.

Referring to FIG. 1, an input light source is shown at block 100. The light source in block 100 can generate any type of electromagnetic radiation. However, the input source will typically be a laser. A laser is used because an optical source of sufficient intensity is desirable to create a nonlinear optical response at the interface to be probed. The type of laser will vary with the particular application and can range from very large, exotic laser systems to extremely small lasers; even a simple diode laser may work in some situations.

The electromagnetic frequency must be one that can be used to access the interface. That is to say, either one or the other or both media (i.e., those that form the interface) must be transparent to the input and output frequencies because the input signal must be transmitted to the interface and the reflected signal must be received from the interface.

Light source 100 could be a single frequency input. However, in a more general case, it will be two input frequencies which could in fact be fixed frequency inputs. Alternatively, one or both of the frequencies could be tunable, that is changeable to different frequency inputs depending on the particular application in question.

5.2 Input Optics

Figure 2:
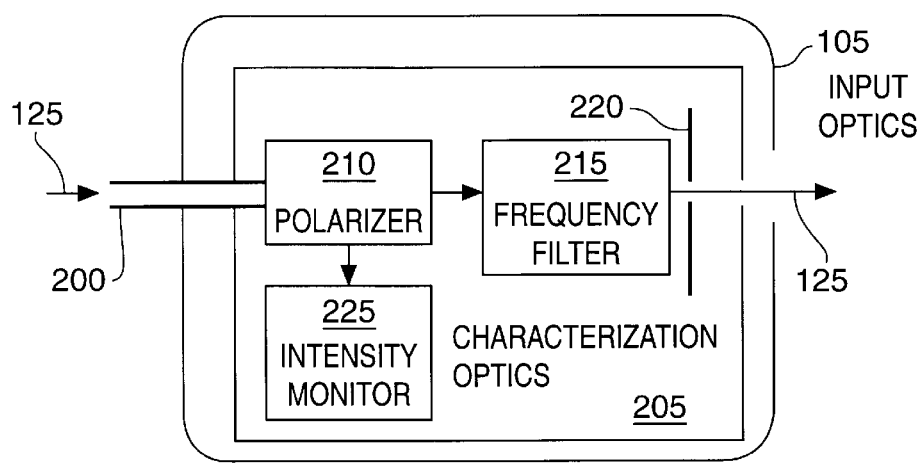
FIG. 2 is a block diagram representation of the input optics shown in FIG. 1.

Input optics 105 function to move light beam 125 and to characterize the light beam. Referring to FIG. 2, transport optics 200 may be used to position and direct the beam. Transport optics 200 may be, for example, fiber optics or other waveguide mechanisms. Alternatively, transport optics 200 may simply be the air or other medium in which the optical beam is traveling (e.g., a vacuum, a liquid, a transparent solid, etc.).

Input optics 105 also include characterization optics 205. Characterization optics 205 function to select a frequency. The one or two input frequencies, are characterized to ensure that only the input frequencies are present and not other frequency components. Other frequency components generated at places other than the surface would mask the signals generated at the surface by the input.

Frequency filter 215 thus filters the light beam to ensure that only the desired frequencies are present. In addition, characterization optics 205 may contain other optional features such as polarizers 210, iris or spatial filters 220, and intensity monitors 225.

Although transport and characterization optics are shown as separated, a system could be designed so that both transport and characterization tasks could be done in a single, specifically designed entity. One example might be a polarization preserving optical fiber. Further, the input fiber might in fact be given frequency selective properties so that in addition to transporting the light, the necessary frequency selection could be performed.

A large number of devices can be used to perform frequency selection. One of the simplest and cheapest of these is a color filter. This is an object that, for instance, will pass only frequencies lower than the input frequency and will generally be opaque to frequencies at harmonics or other higher frequencies. One example of a frequency selective device with better optical properties than a color filter is a holographically designed filter. Other examples include a monochromator or diffraction grating. Virtually any frequency selective or frequency dependent entity could be used as long as the input light is in fact filtered to be composed of only the frequencies which are desired.

5.3 Output Optics

Output optics 115 serves the purpose of transporting the output signal to the detection device and performing the appropriate frequency selection to make sure that the signal which is being detected is in fact the signal that is produced at the interface rather than a spurious signal generated elsewhere (such as at the optical components).

Output optics 115 may be largely the same as input optics 105. The difference primarily is that the input optics are used to direct only the desired input frequencies to the surface. After the light leaves the surface, it is desirable to ensure that the frequency selection device only allows the transmittal of the second-order signal at the output frequency reflected from the interface, such as a second harmonic frequency, sum frequency, or the difference frequency. To accomplish this, frequency selective optics (e.g., color filters, etc.) may be used.

Frequency selection accomplishes two tasks: (1) it makes sure that the detection system sees only the output (reflected) signal desired, and (2) it immediately removes the input frequencies or input fundamentals so that additional frequencies are not produced by the inputs traveling through the subsequent optical components.

As with the input optics, the output optics may optionally include a polarizer and spatial filter. Because the polarization of the output signal may or may not be the same as the polarization of the input signal, the output polarization selective device may or may not be of the same orientation as the input polarization selection device. This will depend upon the particular sample and the particular configuration being used.

5.4 Illustrative Embodiment

Figure 3:
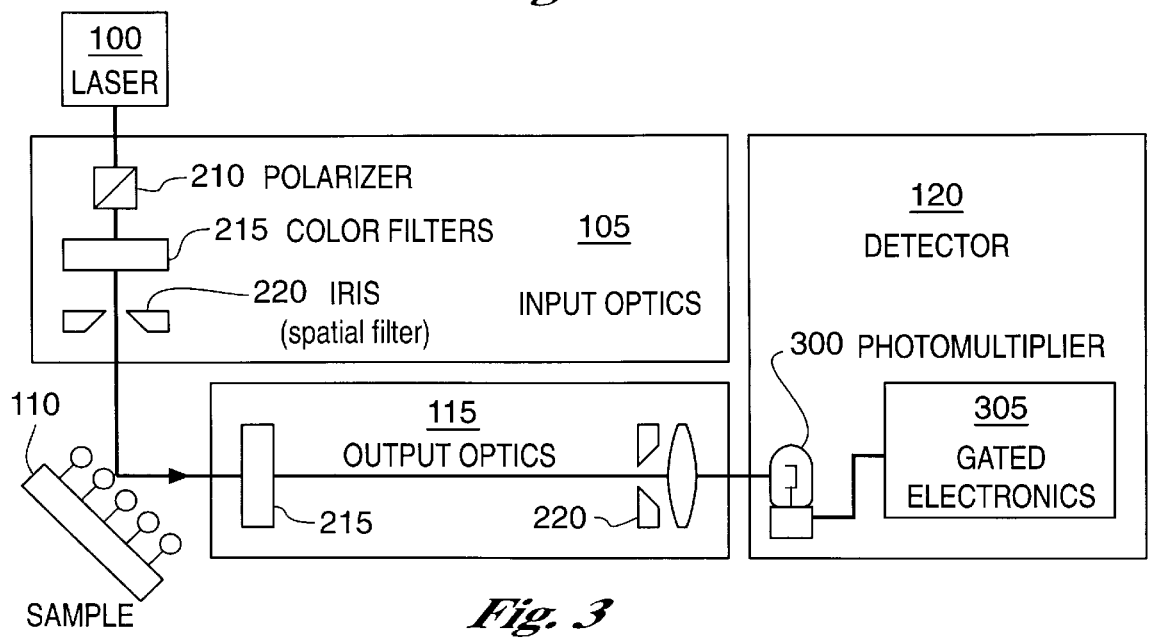
FIG. 3 is a more detailed block diagram representation of the system schematic shown in FIG. 1.

FIG. 3 shows one physical embodiment of the system described in FIG. 1. Laser 100 generates a laser beam which travels through input optics 105 to strike sample 110. The reflected beam travels through output optics 115 and is then detected at detector 120. Input optics 105 include various components and options as discussed with reference to FIG. 2. Output optics 115 also include filter 215 and iris 220. Detector 120 may include photomultiplier 300 and electronics 305.

The signal generated at the interface will typically be of a relatively low light level, perhaps in the one to a few thousand photon level. Consequently, it is desirable to use a detector for low-level light detection such as a photomultiplier. It is also possible to use avalanche photodiodes, which are solid-state analogs of photomultipliers. However, even though these are low-level light detectors, they are "off-the-shelf devices" and may not require any additional engineering other than connection to typical gated integration electronics, in order to be able to measure the electronic response of the detectors after the input radiation is detected.

As shown in FIG. 3, the output signal is reflected off the front of sample 110. However, other configurations are possible. For example, if sample 110 is also transparent (i.e., both media that form the interface are transparent), the output signal may pass through sample 110 and exit the rear of sample 110. Thus, in this case, output optics 15 and detector 120 may be located behind sample 110.

5.5 Input Light Beam Configuration

Referring to FIG. 4A, several possible angles of incidence for a light beam or beams are shown. The input beam shown in the simplest configuration has a single input which is incident to 45° with a subsequent reflected second harmonic output also at 45°. This is one very particular case of the technique.

FIG. 4B illustrates a more general case where there are two beams of frequencies $f_1$ and $f_2$ input at different angles of incidence $\Theta_1$ and $\Theta_2$. In the case where the input beams are at different angles, the reflected beams will be also at different angles and the generated signal such as $f_1+f_2$ will be at another angle different from the $f_1$ and $f_2$ output specular reflections. If, of course, the two input beams are made to be co-linear, then the specular reflections will also be co-linear and the output signal will be co-linear with the two specular reflected beams. This is, however, not the general case.

The two beams do not have to be input from the same side. As shown in FIG. 4C, the inputs can, in fact, come from differing sides of the sample and hit the same spot, which will then mean that the output beam could, in fact, be generated directly away from the surface or possibly at some angle, depending upon the input frequencies $f_1$ and $f_2$ and depending upon the specific optical properties of the interface.

There is one caveat to the preceding generalization, however. The input signal beams can not be normal to the surface. It can be shown that if the inputs are normal to the surface it will not be possible to produce any output signal.

When the two input beams are not co-linear, their reflections will not be co-linear and therefore, the output signal will be at an angle which is different from the two specular reflections. Consequently, in this case the first element in the output optics may be an iris; because output signal will be at a different angle from the two specular reflections, the iris can be positioned in a way that blocks the specular reflections of the fundamentals, while transmitting the output signal. Thus, as shown in FIG. 4B, iris 220 may be used to pass the $f_1+f_2$ reflection while blocking the remaining reflections. So, in this sense, even though this is merely a spatial filter, it is, in fact, doing a first-order frequency selection.

5.6 Calibration

In general, when an experimental apparatus is being set up to do nonlinear optical surface monitoring, frequency responses can be expected in the detector input optics, the output optics, and even the laser itself, which are not to be looked at, in addition to the frequency response arising from the properties of the surface (e.g., surface roughness). Because each of these optics may have a frequency or intensity dependence which is not to be monitored, an external reference/calibration system is desirable for use with the regular optical experimentation set-up.

The reference optics typically will incorporate some optical entity which has a small nonlinear optical response. For example, one could use in transmission a piece of quartz, or in reflection some semiconductor such as Gallium Arsenide with a strong bulk nonlinear optical response. This reference could in one case be temporarily placed directly in the beam path, consequently having the signal measured with the same detection system which is measuring the surface reflection. In this case, the large signal generated by the reference optic is likely to overwhelm the signal from the sample surface and just measure the large reference response. Then, a comparison between the surface signal strength and the reference sample strength is made. From this, it is possible to remove undesired optical changes and make sure that the changes in the signal being measured are due only to the changes occurring at the surface. Alternatively, it is possible to divert part of the input beam or beams to a simulated surface off to the side of the main experimental set-up which can then produce a large signal either in reflection or transmission, and have that large signal sent off to a detection system. In this way, simultaneous reference generation can be obtained at the same time as making a measurement of the surface properties via the nonlinear optical technique.

5.7 Signal Analysis

Signal intensity at detector 120 may be measured as a function of a variety of variables. With reference to FIG. 5, the intensity (I), of detected signal 500 is shown to vary with the sample position (d).

The graph shows the intensity of the detected signal as a function of position on a given surface or interface. In this case, differing chemical or physical characteristics of the surface result in a change in the intensity of the detected signal as different locations of the surface are analyzed. This change in the amount of signal strength indicates that there are different chemical or physical properties of the interface at different positions of the surface.

FIG. 5A illustrates the intensity (I) of a detected signal varying with respect to time (t). In signal 505 a certain interface parameter (e.g., a chemical or physical property) has been changed or is intentionally being changed as a function of time. As the specific properties of the interface vary with time, the intensity of the detected signal will vary with time. This is shown in FIG. 5B as a time varying plot of intensity.

FIG. 5B illustrates yet another example of the intensity of the detected signal changing. In this case, the intensity of detected signal 510 varies as a function of frequency (f). It specifically varies as a function of the input frequency similar to classical linear absorption spectroscopy where the intensity of light is measured by the amount of transmission through material. In this figure, the intensity (I) of the output signal is seen as a function of the frequency (f) of the input signal. As different chemical processes occur at the interface, they will lead to a modification of the spectral response of the interface. This leads to a modification of the spectral intensity of the output signal as a function of the input signal's frequency.

In one embodiment, the input frequency may be changed by using two input lasers. Preferably, one laser has a fixed frequency, the second laser has a tunable frequency, and the detected signal is the sum frequency of the two laser frequencies used. In another embodiment, the fixed frequency is in the visible range and the tunable frequency is in the infrared range. Thus, the frequency of the detected signal is a function of the tunable frequency and a spectrum of output signals may be detected as the tunable frequency is changed.

In addition to intensity and spectral changes, there can at times be a desire to measure polarization dependence of the input and output signals as a function of whatever surface characteristics are being changed. Specifically, through the nature of the nonlinear optical process at the interface, for a given input polarization only certain output polarization combinations can be produced. Violation of these polarization combinations can lead one to determine what specific mechanical, physical, or molecular orientation properties are occurring on the surface as a given characteristic of the surface is being modified.

5.8 Liquid Crystal or Polyimide Thin Film Monitoring

In another embodiment, the techniques discussed above can be used to monitor the binding and alignment of a thin film of liquid crystal or polyimide material in a liquid crystal display. When an item which is of a thin film nature is manufactured, the surface properties become increasingly more important. If the film were one molecular layer thick, the surface properties would govern the physics of the entire device. Even though many thin films may be multilayered, some are still thin enough that the surface properties have a strong effect on the quality and behavior of the interior bulk. Thus, the surface alignment of the molecules, as well as how strongly they are bonded to the surface, become increasingly important in determining the quality of the device being fabricated.

The alignment of the molecules of liquid crystal or polyimide material affects, and therefore can be determined by measuring changes in, the polarization of the second harmonic with respect to the relative alignment of the molecules on the surface. As will be apparent to those of ordinary skill in the art, polarization (specifically the axis of polarization 600) typically relates to the orientation of the electric field 605 of the radiation of interest as shown in FIG. 6. Polarizing elements (e.g., polarizing sunglasses 610) are typically designed to pass radiation whose electric field 615 is parallel to the polarizing axis 620 of the element 610 and block radiation whose electric field 625 is perpendicular, or normal, to the polarizing axis 620.

FIG. 7 shows a cross sectional view of a thin film of liquid crystal or polyimide material 705 on a multilayered liquid crystal display 700. The alignment of a thin film typically comprises the angle the molecules 710 of the thin film 705 make with a normal to the surface 720 (i.e., surface normal) and the degree of anisotropy (i.e., degree to which the molecules point in a net direction). For example, molecules of the thin film which have no anisotropy will exhibit essentially no net change in polarization dependence on the angles of incidence (i.e., the $\Theta$ and $\phi$ of the incident radiation relative to the surface normal) of the laser light or other directed radiation as the sample is rotated about the surface normal. That is to say, as the thin-film sample is rotated, the intensity of the light passing through the output polarizer will change only when the molecules of the sample possess a net anisotropy. As a result, the degree of change in polarization as the sample is rotated can be used to determine the alignment of the molecules on the thin film.

The binding of the molecules to the surface can also be determined with a method in accordance with the invention. A tunable light source can be used to make a spectroscopic measurement of the surface under consideration. Resonances can result from the incoming radiation encountering molecular bonds. These resonances contain valuable bonding information and can indicate how the atoms are bonded together and how the molecules are bonded to the surface.

FIG. 8A illustrates molecules with an internal bond of $\Gamma$ that are located near the surface but do not have any direct bonding with the surface. As shown in FIG. 8B, a sum frequency generation spectrum of these molecules would result in a resonance with one peak at a frequency of $\Gamma$. In contrast, molecules that have a direct bond of $\gamma$ with the surface (see FIG. 8C) and an internal bond $\Gamma$ produce a sum frequency generation spectrum with two resonances (see FIG. 8D). The first resonance centered at a frequency of $\Gamma$ identifies the molecule in question, while the second resonance centered at a frequency of $\gamma$ indicates that the molecule has formed a new bond (i.e., not in the orginal molecule) with the surface. This new resonance for the $\gamma$ bond signifies the quality of the molecular bonding with the surface.

Monitioring of a thin film of liquid crystal of polyimide material provides information on the binding and alignment of molecules with the surface. As will be apparent to those of ordinary skill in the art having the benefit of this disclosure, knowledge of the binding and alignment of the molecules in a liquid crystal or polyimide material with the surface can be used to provide additional information about the surface properties of the material.

It will be appreciated by those of ordinary skill in the art having the benefit of this disclosure that numerous variations from the foregoing illustration will be possible without departing from the inventive concept described therein. Accordingly, it is the claims set forth below, and not merely the foregoing illustration, which are intended to define the exclusive rights claimed in this application program.

What is claimed is:

1. A method of monitoring the properties, including binding characteristics and molecular alignment, of a surface of a thin film of polyimide material, where the surface is an interface between the thin film of polyimide material and a different media, and where the thin film of polyimide material is in a liquid crystal display, comprising:

a) directing at least two simultaneously-generated laser beams to an area of the thin film surface, wherein each of said at least two laser beams is directed through an input filter which attenuates frequencies higher than a fundamental frequency of a specified one of said at least two laser beams;

b) passing a respective reflection of each of said at least two laser beams from said thin film surface through an output filter which attenuates frequencies lower than a sum frequency of said at least two laser beams; and c) monitoring the intensity of said sum frequency.

2. The method of claim 1, one of said laser beams being at a fixed visible frequency and one of said laser beams being at a tunable infrared frequency.

3. A method of in situ monitoring the properties, including binding characteristics and molecular alignment, of a surface of a thin film of polyimide material, where the surface is an interface between the thin film of polyimide material and a different media, and where the thin film of polyimide material is in a liquid crystal display, comprising:

a) directing electromagnetic radiation, referred to as directed radiation, to an area of the thin film surface; and b) monitoring a parameter of electromagnetic radiation, referred to as second-order radiation, generated by a second-order radiation response of the thin film surface to the directed radiation, said parameter being referred to as a second-order parameter, wherein said second-order parameter varies with said alignment and the degree of anisotropy of said thin film surface.

4. The method of claim 3, wherein the second-order radiation response is a reflection of the directed radiation from the interface.

5. The method of claim 4, wherein said second-order parameter comprises an intensity parameter of said reflection.

6. The method of claim 4, wherein said reflection passes through a polarization-sensitive element.

7. The method of claim 3, wherein said second-order parameter varies as a function of the frequency of said directed radiation.

8. The method of claim 3, wherein said directing operation comprises directing electromagnetic radiation from a single source of radiation.

9. The method of claim 3, wherein said second-order radiation has a frequency that is a second harmonic of said single source of radiation.

10. The method of claim 3, wherein said directing operation comprises directing electromagnetic radiation from a plurality of sources of simultaneously-generated radiation.

11. The method of claim 10, wherein a first one of said plurality of sources of radiation emits radiation at a frequency different from that of a second one of said plurality of sources of radiation.

12. A method of monitoring the properties, including binding characteristics and molecular alignment, of a surface of a thin film of polyimide material, where the surface is an interface between the thin film of polyimide material and a different media, and where the thin film of polyimide material is in a liquid crystal display, comprising:

a) directing electromagnetic radiation, referred to as directed radiation, to an area of the thin film surface; and b) monitoring an intensity parameter of electromagnetic radiation, referred to as second-order radiation, generated by reflection of said directed radiation from the thin film surface, wherein said intensity parameter changes in the presence of a polarization of said electromagnetic radiation.

13. The method of claim 12, wherein said polarization is elliptical.

14. The method of claim 12, wherein said polarization is linear.

15. The method of claim 12, wherein said polarization is circular.

16. A method of detecting change in the properties, including binding characteristics and molecular alignment, of a surface of a thin film of polyimide material, where the surface is an interface between the thin film of polyimide material and a different media, comprising:

a) directing at least one laser beam to an area of the thin film surface, wherein each of said at least one laser beam is directed through an input filter which attenuates frequencies higher than a fundamental frequency of a specified one of said at least one laser beam;

b) passing a respective reflection of each of said at least one laser beam from said thin film surface through an output filter which attenuates frequencies lower than a specified frequency; and c) monitoring the intensity of said specified frequency, said specified frequency being a second-order frequency.

17. The method of claim 16, wherein said specified frequency is a second harmonic of said fundamental frequency.

18. The method of claim 16, wherein (i) the at least one laser beam comprises two or more laser beams generated substantially simultaneously, and (ii) said specified frequency is a sum frequency or a difference frequency of two of said simultaneously-generated laser beams.

19. A program storage device readable by a machine and encoding a program of instructions for performing the method steps of a specified one of claims 1 through 18.

* * * * *